(12) United States Patent
Hiemer et al.

(10) Patent No.: US 10,335,249 B2
(45) Date of Patent: Jul. 2, 2019

(54) SYRINGE FOR MULTI-COMPONENT MATERIALS, METHOD OF ACTIVATING A SYRINGE, MIXING AND DISPENSING APPARATUS AND MULTI-COMPONENT CARTRIDGE

(71) Applicant: Sulzer Mixpac AG, Haag (CH)

(72) Inventors: Andreas Hiemer, Rebstein (CH); Marco Zünd, Widnau (CH)

(73) Assignee: SULZER MIXPAC AG, Haag (CH)

(*) Notice: Subject to any disclaimer, the term of this patent is extended or adjusted under 35 U.S.C. 154(b) by 44 days.

(21) Appl. No.: 15/321,423

(22) PCT Filed: Jun. 19, 2015

(86) PCT No.: PCT/EP2015/063833
§ 371 (c)(1),
(2) Date: Dec. 22, 2016

(87) PCT Pub. No.: WO2015/197492
PCT Pub. Date: Dec. 30, 2015

(65) Prior Publication Data
US 2017/0156820 A1    Jun. 8, 2017

(30) Foreign Application Priority Data

Jun. 23, 2014 (EP) .................................... 14173481

(51) Int. Cl.
*A61C 5/64* (2017.01)
*B01F 13/00* (2006.01)
(Continued)

(52) U.S. Cl.
CPC .............. *A61C 5/64* (2017.02); *A61C 9/0026* (2013.01); *B01F 5/0077* (2013.01);
(Continued)

(58) Field of Classification Search
CPC ....... A61C 5/64; A61C 9/0026; B01F 5/0077; B01F 5/0618; B01F 13/0023;
(Continued)

(56) References Cited

U.S. PATENT DOCUMENTS 3,767,085 A    10/1973    Cannon et al.
4,050,676 A    9/1977    Morishima et al.
(Continued)

FOREIGN PATENT DOCUMENTS

DE    102007044983 A1    4/2009
EP    0669113 A2    8/1995
(Continued)

*Primary Examiner* — Paul R Durand
*Assistant Examiner* — Andrew P Bainbridge
(74) *Attorney, Agent, or Firm* — Global IP Counselors, LLP

(57) ABSTRACT

A syringe for multi-component materials includes a mixer housing, a mixing element, a multi-component cartridge and a mixing head, the mixing head being arranged at least partly within the mixer housing and adjacent to the multi-component cartridge. The mixing head is arranged moveable in an axial direction of the syringe between at least two positions, the at least two positions including a sealed position and a dispensing position. The axial movement of the mixing head is brought about by rotation of at least a part of the mixer housing relative to the multi-component cartridge. The mixing head is axially displaced in a direction opposite to a dispensing direction on a displacement of the mixing head from the sealed position into the dispensing position.

29 Claims, 9 Drawing Sheets

(51) Int. Cl.
  *B05C 11/10* (2006.01)
  *B01F 5/06* (2006.01)
  *B01F 15/00* (2006.01)
  *B05C 17/005* (2006.01)
  *A61C 9/00* (2006.01)
  *B01F 5/00* (2006.01)

(52) U.S. Cl.
  CPC ........ *B01F 5/0618* (2013.01); *B01F 13/0023* (2013.01); *B01F 15/0087* (2013.01); *B05C 11/1031* (2013.01); *B05C 17/00553* (2013.01); *B05C 17/00593* (2013.01); *B01F 2215/006* (2013.01); *B01F 2215/0027* (2013.01)

(58) Field of Classification Search
  CPC .......... B01F 15/0087; B01F 2215/0027; B01F 2215/006; B05C 11/1031; B05C 17/00553; B05C 17/00593
  USPC .......... 222/145.5–145.6, 135–140, 325–327, 222/391, 502–503, 531, 560; 604/89, 91
  See application file for complete search history.

(56) References Cited

U.S. PATENT DOCUMENTS

| | | | |
|---|---|---|---|
| 4,771,919 A * | 9/1988 | Ernst | B65D 81/325 222/134 |
| 5,033,650 A | 7/1991 | Colin et al. | |
| 5,122,117 A | 6/1992 | Haber et al. | |
| 5,722,829 A | 3/1998 | Wilcox et al. | |
| 6,352,177 B1 | 3/2002 | Bublewitz et al. | |
| 6,398,761 B1 | 6/2002 | Bills et al. | |
| 6,601,782 B1 | 8/2003 | Sandholm et al. | |
| 6,613,021 B2 * | 9/2003 | Sogaro | A45D 19/02 604/191 |
| 6,698,622 B2 | 3/2004 | Sawhney et al. | |
| 7,383,969 B2 | 6/2008 | Horth et al. | |
| 7,874,458 B2 * | 1/2011 | Sogaro | B05C 17/00506 222/137 |
| 8,770,451 B2 * | 7/2014 | Vogt | A61B 17/8822 222/137 |
| 9,522,368 B2 * | 12/2016 | Bublewitz | A61M 5/31596 |
| 2005/0226095 A1 | 10/2005 | Wagner et al. | |
| 2006/0014440 A1 * | 1/2006 | Sogaro | A61C 9/0026 439/652 |
| 2007/0166660 A1 * | 7/2007 | Peuker | A61B 17/00491 433/89 |
| 2007/0175921 A1 * | 8/2007 | Keller | B05C 17/00506 222/137 |
| 2008/0083782 A1 | 4/2008 | Heusser et al. | |
| 2008/0195082 A1 * | 8/2008 | Pauser | A61C 9/0026 604/518 |
| 2008/0287880 A1 | 11/2008 | Keller | |
| 2008/0314929 A1 * | 12/2008 | Keller | B05C 17/00506 222/145.6 |
| 2010/0206904 A1 | 8/2010 | Staub et al. | |
| 2010/0330525 A1 | 12/2010 | Grundler et al. | |
| 2011/0114668 A1 | 5/2011 | Bublewitz et al. | |
| 2011/0272436 A1 | 11/2011 | Vogt et al. | |
| 2012/0187148 A1 | 7/2012 | Ettlin et al. | |
| 2012/0228329 A1 * | 9/2012 | Staub | B65D 81/325 222/137 |
| 2013/0177870 A1 | 7/2013 | Wang et al. | |
| 2014/0117041 A1 | 5/2014 | Springhorn | |
| 2015/0216577 A1 * | 8/2015 | Vogt | A61B 17/8833 366/76.7 |
| 2015/0291339 A1 | 10/2015 | Leue | |
| 2017/0156820 A1 * | 6/2017 | Hiemer | B05C 17/00593 |

FOREIGN PATENT DOCUMENTS

| | | |
|---|---|---|
| EP | 0121342 A2 | 10/1998 |
| EP | 1925370 A1 | 5/2008 |
| EP | 2266649 A1 | 12/2010 |
| WO | 2006005206 A1 | 1/2006 |
| WO | 2008113196 A1 | 9/2008 |
| WO | 2010108868 A1 | 9/2010 |
| WO | 2014063848 A1 | 5/2014 |

* cited by examiner

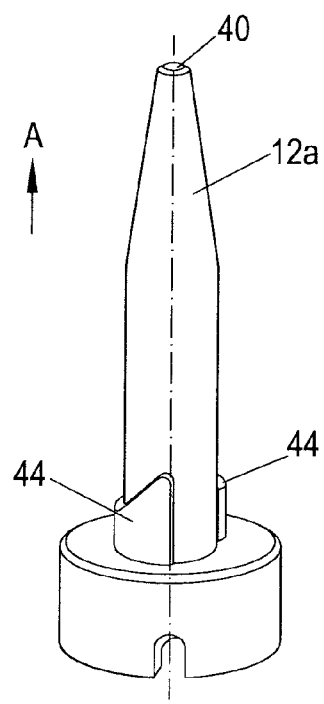
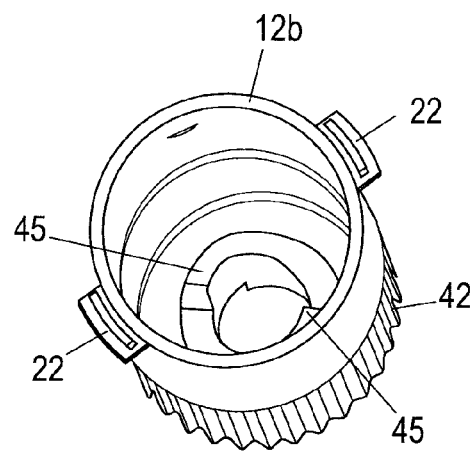
Fig. 5A
Fig. 5B
Fig. 6
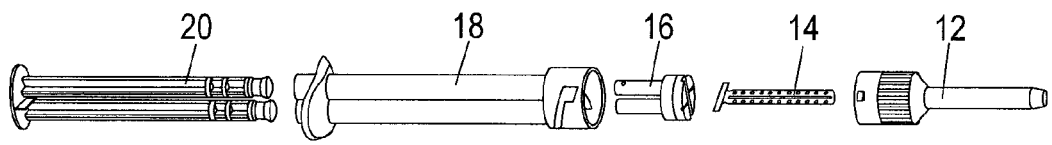

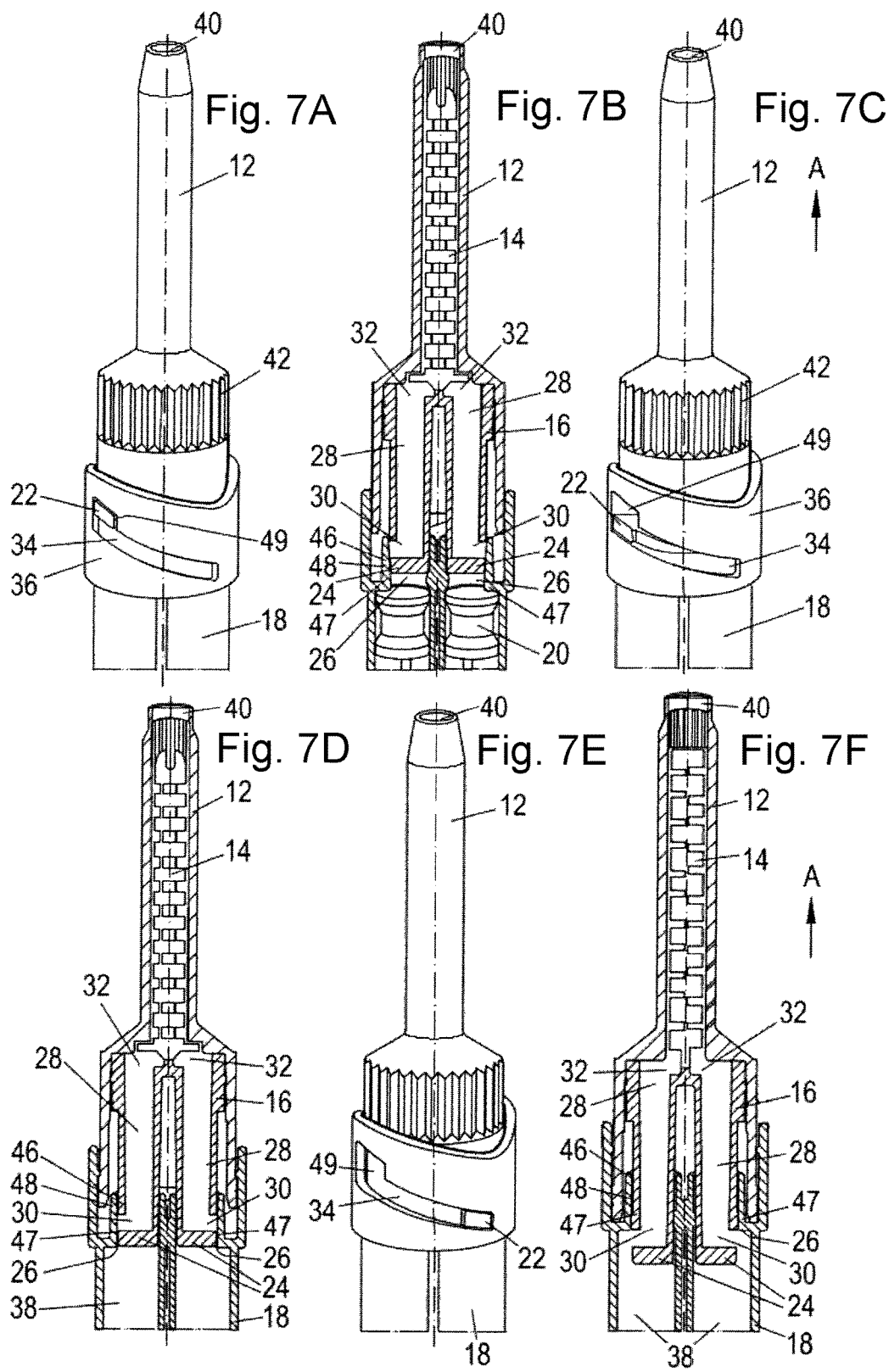

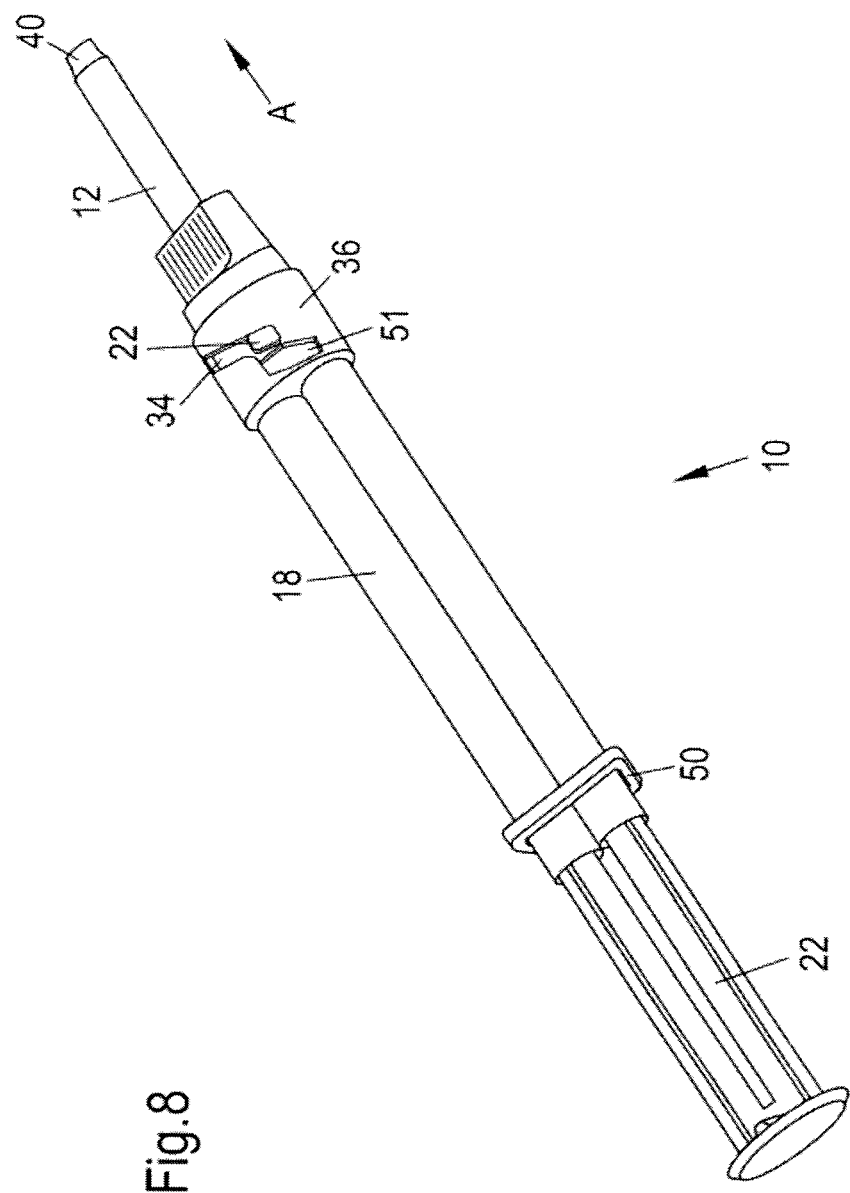

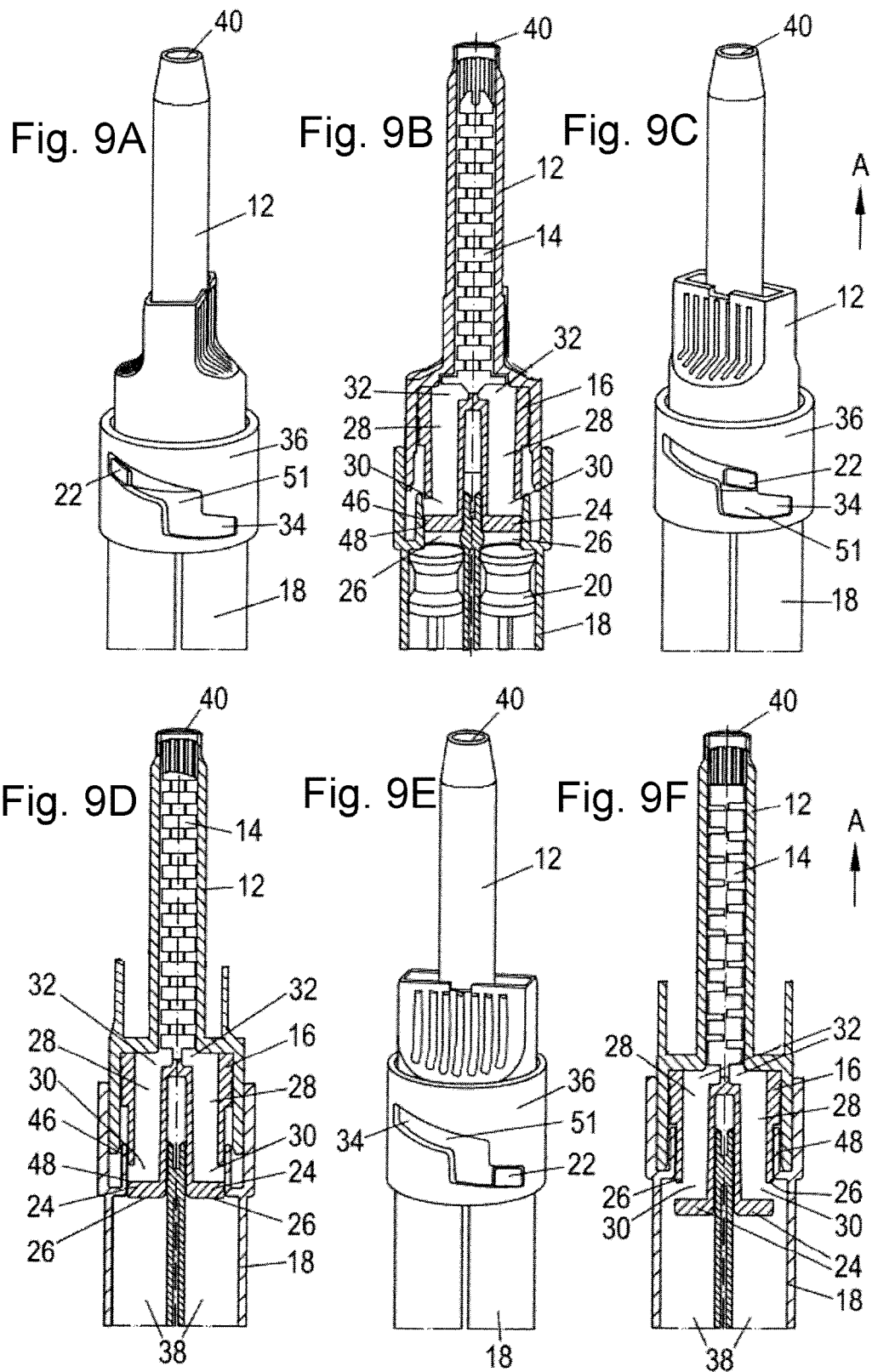

SYRINGE FOR MULTI-COMPONENT MATERIALS, METHOD OF ACTIVATING A SYRINGE, MIXING AND DISPENSING APPARATUS AND MULTI-COMPONENT CARTRIDGE

CROSS-REFERENCE TO RELATED APPLICATIONS

This application is a U.S. National Stage application of International Application No. PCT/EP2015/063833, filed Jun. 19, 2015, which claims priority to EP Application No. 14173481.4, filed Jun. 23, 2014 the contents of each of which is hereby incorporated herein by reference.

BACKGROUND

Field of Invention

The invention relates to a syringe for multi-component materials, preferably a single-fill syringe for multi-component materials, to a method of activating a syringe, to a mixing and dispensing apparatus and to a multi-component cartridge.

Background Information

Common syringes are simple pumps which are typically used for the metering of small amounts of material and generally comprise a tube for the material to be metered, a plunger that fits tightly into the tube and by means of which a material present in the tube can be discharged via a needle or nozzle attached at the opposite end of the syringe. The tube is frequently also used as a storage chamber for materials.

Syringes for multi-component materials also exist. The materials to be dispensed are typically a matrix material and a hardener. The filled cartridges come in different sizes referred to as 1:1, 2:1, 4:1 and 10:1 etc., the numbers specifying the ratios of the amounts of each of the two materials that are to be dispensed. The reason for these different sizes is to allow a wide variety of different compositions to be mixed and dispensed. For example some compositions require more hardener and some require less hardener. Also some compositions require more mixing.

Two-component materials are typically used as impression materials, e.g. on the formation of dental impressions, such impression material is e.g. sold under the tradename Affinis, as a cement material for prosthetic restorations, e.g. sold using the tradename Per-maCem, as a temporary cement for trial cementing restorations or for cementing temporary crowns, e.g. sold using the tradename Temp-Bond. Further applications of two-component materials are in the building industry where they are e.g. used as a replacement for mechanical joints that corrode over time. Adhesive bonding can be used to bond products such as windows and concrete elements. The use of multi-component protective coatings, for example moisture barriers, corrosion protection and anti-slip coatings, is also becoming increasingly common.

Dispensing apparatus for multi-component materials are also known and range from multiple application devices if they are used in combination with e.g. replaceable mixing tips, to single application devices. On discharging these multi-component materials, the different components have to be combined with one another in order for these to react.

Two-component materials are known, for example in the dental field or in the building sector. The two-component materials typically only cure when they come into contact with one another. However, these components are chemical compositions and can degrade if they are exposed to air for a considerable period of time. For this reason pre-filled syringes and cartridges have to be provided with a closure which prevents the materials from premature aging and which ensure a certain storage life of the components. This storage capability must nevertheless be easily accessible on a dispensing of the materials. For one time applications the closure need not be re-sealable for multiple dispensing applications the closure has to be re-sealable.

SUMMARY

For this reason it is an object of the present invention to provide a syringe having a dispensing assembly which is both easily accessible and which ensures a good seal with respect to the storage of the multi-component materials stored therein.

This object is satisfied by a syringe in accordance with the invention.

A syringe for multi-component materials, preferably for two-component materials, thus comprises a mixer housing, a mixing element, a multi-component cartridge, such as a two-component cartridge, and a mixing head, the mixing head being arranged at least partly within the mixer housing and adjacent to the multi-component cartridge, wherein the mixing head is arranged moveable in an axial direction of the syringe between at least two positions, the at least two positions comprising a sealed position and a dispensing position, wherein the axial movement of the mixing head is brought about by a rotation of at least a part of the mixer housing relative to the multi-component cartridge, and wherein the mixing head is axially displaced in a direction opposite to a dispensing direction on a displacement of the mixing head from the sealed position into the dispensing position.

Such a syringe provides a user with a pre-filled syringe which can easily be activated, this means that e.g. outlets of the cartridge can easily be opened in order to allow a dispensing of materials present in respective chambers of the multi-component cartridge. The activation of the syringe can simply take place by a rotation of at least a part of the mixer housing from a sealed position into a dispensing position. This can be achieved in that passages possibly present in the mixing head are made accessible in the dispensing position thus permitting access of materials present in the cartridge to the syringe outlet.

In this connection a sealed position means a position in which the multi-component cartridge is sealed and materials, i.e. substances, possibly present in chambers of the multi-component cartridge cannot exit this. This means that the syringe cannot be used to dispense materials in the sealed position.

It should also be noted that the dispensing position is a position in which the materials can be discharged out of the cartridges, for example by respective dispensing pistons or a plunger assembly adapted to move in the cartridges in order to dispense the materials out of the cartridges and the syringe via the mixer housing and the mixing element.

It should further be noted in this connection that a syringe for multi-component materials means a syringe which can be used with two-component materials, three component materials etc.

The rotational movement of the mixer housing relative to the cartridge also ensures that, on an actuation of the plunger in the dispensing direction, the mixing head does not inadvertently axially move back into the sealed position during the dispensing. This is because the axial movement is brought about by a rotation and not just simple axial movement.

Axially displacing the mixing head in a direction opposite to a dispensing direction on displacement of the mixing head from the sealed position into the dispensing position, enables the mixing head—through which a dispensing of multi-component materials preferably takes place in the dispensing position—to be brought into an, in particular flow communicating, contact with the multi-component materials present in the multi-component cartridge so as to facilitate a dispensing of materials from the multi-component cartridge via the mixing head.

In this connection it should be noted that a direction opposite to a dispensing direction is an axial direction in which the mixing head is moved towards the multi-component cartridge.

It is preferred if the mixing and dispensing apparatus, for example comprising the mixer housing, the mixing element and the mixing head, is attached to the multi-component cartridge after this has been filled. In such an assembly no venting means (or devices) are required on filling of the cartridge with the materials to be stored and dispensed. In such an assembly the apparatus can simply be snapped on to the cartridge and it may be preferable if this cannot be removed once it is attached.

Preferably the mixing head at least partly projects into the multi-component cartridge in the dispensing position.

This advantageously means that, through the axial displacement of the mixing head towards the multi-component cartridge, a pressure on materials stored within the multi-component cartridge—in a filled state thereof—is momentarily increased shortly before the mixing head is in the dispensing position and this slight increase in pressure then facilitates the flow of materials out of the multi-component cartridge via the mixing head.

It is preferred when at least a part of a base of the mixing head is formed as a seal and seals outlets of the multi-component cartridge. Thereby the syringe requires fewer components and can be produced in a more cost effective manner.

In an advantageous embodiment the mixing head comprises a plurality of passages, preferably two or more substantially L-shaped passages in a cross-section thereof, for the multi-component materials to be dispensed, wherein a material to be dispensed can only enter the passages when the mixing head is in the dispensing position, preferably through the short shank of the substantially L-shaped passage.

Such a construction ensures that the base of the mixing head can be formed as a seal without additional parts being required to ensure a seal in the region of the base of the mixing head and therefore in the region of the outlets. Moreover, such a manner of construction permits a good access of materials present in the chambers of the cartridges into the dispensing part of the syringe.

Advantageously each of the passages of the mixing head projects at least partly into a respective chamber of the multi-component cartridge in the dispensing position to form a fluid connection between the passages and the chambers.

This ensures a fluid connection between the passages and the chambers and thereby a material flow from the chambers into the passage and thus through the syringe when the syringe has been activated, by moving the mixing head axially into its dispensing position, and the plunger is actuated.

In a further embodiment the mixing head comprises a mixing portion connecting the two passages and permitting a fluid flow to the mixing element, with the two-components preferably coming into contact with one another in the region of the mixing element down-stream of the mixing portion.

In this way the materials from the multi-component cartridges can be combined so that an effective mixing of the materials present in the cartridges can take place. Moreover, having a defined start of the mixing region in the vicinity of the mixing portion can also help the definition of a size of the mixing element required to mix two or more components. This size of the mixing element, i.e. a length and/or a diameter of the mixing element, is defined by the materials to be mixed, this typically depends on the viscosity of the components, as well as further properties of the components, i.e. how these interact with one another.

It can be advantageous when the mixer housing is non-releasably connected to the multi-component cartridge. This design is particularly useful to ensure that a seal of the outlets of the multi-component cartridge cannot be broken once the syringe has been filled.

In a preferred embodiment the mixer housing is connected to the multi-component cartridge by means of a bayonet like connection or a snap on type connection. These types of connections can ensure a correct placement of the mixer housing relative to the multi-component cartridge. Moreover, such connections can be carried out in a non-releasable manner.

It should also be noted in this connection that the connection between the multi-component cartridge and the mixer housing has some form of alignment mechanism to further ensure a correct rotational orientation between these elements. This is in particular true for multi-use syringes, where a wrong placement of the mixer housing and thus of the dispensing mechanism onto the cartridge can lead to the components present in the cartridges being cross contaminated and the syringe thereby becomes unusable. This is particularly problematic in the case of dental adhesives which are generally very costly.

In a preferred embodiment, rotation of the mixer housing brings about axial displacement of at least a part of the mixer housing and the mixing head relative to the multi-component cartridge.

This axial displacement ensures that the mixing head can be moved between the at least two positions by axial displacement. This is particularly beneficial when the mixing head comprises passages which are only accessible when the mixing head projects at least partly into respective chambers of the multi-component cartridge in the dispensing position to form a fluid connection between the passages and the chambers. This ensures a fluid connection between the passages and the chambers and thereby a material flow from the cartridge into the passage and through the syringe when the syringe has been activated.

Moreover, this design can be realized particularly simply by compulsory guidance which forces at least a part of the mixer housing and the mixing head to be axially displaced on a rotation of at least a part of the mixer housing relative to the multi-component cartridge. This compulsory guidance can e.g. be formed by a cam cooperating with a slot.

In a further preferred embodiment the mixer housing is an at least two-part housing, with the two parts being axially moveable with respect to one another, with the axial movement preferably being effected by means of cooperating ramps present at each of the two parts. This form of compulsory guidance can ensure that the mixing head is displaced from the sealed position into the dispensing position.

In yet a further preferred embodiment the mixing head can be provided in a further axial position, a venting position, with the venting position preferably being provided for a filling of the two-component cartridge.

In this connection it must be noted that a venting position is a position in which at least a part of the syringe has to be vented, e.g. on a filling of the syringe, to ensure that air present in the syringe is permitted to leave the syringe. This is in particular important when air has a negative effect on the substance being stored in the cartridges of the syringe. Such a venting can increase a shelf lifetime of the syringe including the materials.

Such a venting position is in particular required if the multi-component cartridge is to be filled from the end remote of the mixing head, since in this case the materials to be stored in the multi-component cartridge are introduced from that end and air present in the cartridge has to be allowed to be removed.

In an advantageous embodiment, elements are provided preventing movement of the mixing head from the dispensing position into the sealed position, with the elements preferably being selected from the group of members comprising pins, predetermined breaking points, bars and ramps or a combination of these members. Similar elements can also be provided ensuring that a movement of the mixing head from the sealed position into the venting position is prevented.

In this connection it should be noted that means (or devices) can also be provided which maintain the syringe in the sealed position during a storage and transport thereof. These devices can be in the form of webs which bridge a guide portion of the cartridge and prevent an accidental rotation of the mixer housing from the sealed position into the dispensing position. On an application of the correct pressure these webs break and permit the rotational movement of the mixer housing.

These kind of elements are beneficial to ensure that a syringe has not been used, i.e. that a cross contamination or a different source of contamination has not been brought about, so that the desired mixing of the components present in the syringe can be achieved. Such elements are in particular useful then when the syringe is configured as a single use syringe, since these prevent the syringe from being repositioned such that it could be used again.

Advantageously the movement of the mixing head from the venting position into the sealed position is effected by at least one of an axial movement of at least a part of the mixer housing and a rotation of the mixer housing relative to the multi-component cartridge.

This possibly two stage movement can ensure that the seal required to effectively seal the chambers of the multi-component cartridge is engaged in a correct manner. Moreover, this two stage process may also enable the elements preventing the syringe from being repositioned from the sealed position into the venting position to be correctly engaged, improving the storage safety of the syringe.

Axial movement of the part of the mixer housing can be provided to either engage or disengage the sealed position. This is particularly important if the sealed position is brought about by a press fit between the outlet of the cartridge and the base of the mixing head.

It is preferred when the multi-component cartridge is filled with substances. In this way syringes can be filled in a factory under predefined conditions and excess sources of contamination can more easily be avoided.

In a preferred embodiment the syringe further comprises a guide portion having at least one guide slot associated with the multi-component cartridge, the guide portion preferably being fixedly connected to or integrally formed with the multi-component cartridge, and wherein the mixer housing includes at least one cam cooperating with the at least one guide slot in order to facilitate the rotational and/or axial movement between the sealed position and the dispensing position or between the venting position, the sealed position and the dispensing position.

In this connection it must be noted that the at least one guide slot could also be disposed at the mixer housing and the at least one cam can be disposed at the guide portion.

This slot and cam cooperation ensures a simple activation of the syringe as the compulsory guidance provided thereby is predefined and only allows the movement of at least a part of the mixer housing in a predefined manner, e.g. within the slot. This facilitates the ease of use of the syringe in order to activate this and to subsequently dispense the materials from the multi-component cartridge.

This sort of cooperating mechanism is also known as a compulsory guide.

Such guide slots can have the following preferred shapes: a straight slot running generally perpendicular to a dispensing direction of the syringe, a straight slot running at an inclination to the dispensing direction, a slot having at least one axial jump and combinations of such slots.

In an aspect of the invention this relates to a method of activating a syringe, wherein at least a part of a mixer housing of the syringe is rotated relative to a multi-component cartridge in order to bring about an axial displacement of a mixing head from a sealed position into a dispensing position, and a subsequent dispensing of flowable substances present in the multi-component cartridge by pushing a plunger to discharge the flowable substances through the mixer housing via the mixing head and via a mixing element.

Such a method provides an easy to handle method of activating a syringe in order to be able to dispense multi-component materials stored therein in a fast and efficient manner.

In a further aspect of the invention this relates to a mixing and dispensing apparatus for multi-component materials, the apparatus comprising a mixer housing, a mixing element, and a mixing head, the mixing head being arranged at least partly within the mixer housing and the mixing and dispensing apparatus being configured to be connected to a multi-component cartridge and the mixing head is configured to be moveable in an axial direction of the mixing and dispensing apparatus between at least two positions when the mixing head is connected to the multi-component cartridge, the at least two positions comprising a sealed position and a dispensing position, wherein the axial movement of the mixing head is brought about by a rotation of at least a part of the mixer housing relative to the multi-component cartridge when this is connected to the mixing and dispensing apparatus.

In yet a further aspect of the invention this relates to a multi-component cartridge, the cartridge comprising a connection device being configured to be connected to a mixing and dispensing apparatus and a mixing head of the mixing and dispensing apparatus being configured to connect the cartridge to the mixing and dispensing apparatus so that the mixing head of the mixing and dispensing apparatus is moveable in an axial direction of the multi-component cartridge between at least two positions when the mixing head is connected to the multi-component cartridge via the connection device, the at least two positions comprising a sealed position and a dispensing position, wherein the axial movement of the mixing head is brought about by a rotation of at least a part of a mixer housing of the mixing and dispensing apparatus relative to the multi-component cartridge when this is connected to the mixing and dispensing apparatus via the connection device.

In this connection it should be noted that the features described in detail in connection with the syringe can also be provided at such a mixing and dispensing apparatus and also at such a cartridge.

BRIEF DESCRIPTION OF THE DRAWINGS

Referring now to the attached drawings which form a part of this original disclosure.

FIGS. 5A-5B are a multi part mixer housing;

FIG. 6 is an exploded view of a further embodiment of a syringe;

FIGS. 7A-7F are different positions of use of the syringe of FIG. 6;

FIG. 8 a view of a further embodiment of a syringe;

FIGS. 9A-9F are different positions of use of the syringe of FIG. 8;

DETAILED DESCRIPTION OF THE EMBODIMENTS

Figure 1:
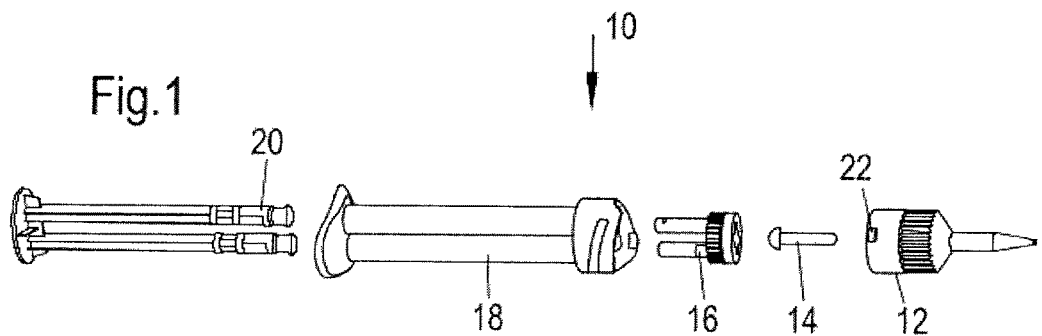
FIG. 1 is an exploded view of a first embodiment of a syringe.

Features which have the same or a similar function will be described in the following using the same reference numeral. It is also understood that the description given with respect to reference numerals used in one embodiment also applies to the same reference numerals in connection with other embodiments unless something is stated to the contrary.

FIG. 1 shows an exploded view of a first embodiment of a syringe 10. The syringe 10 comprises a mixer housing 12, a mixing element 14, such as a static mixer, a mixing head 16, a two-component cartridge 18 and a plunger 20. On assembly of these components (see e.g. FIGS. 2A and 2C) the mixing element 14 is received in the mixer housing 12 adjacent to the mixing head 16 which in turn is partly received in the mixer housing 12 and is arranged adjacent to the two-component cartridge 18. The mixer housing 12 is attached to the two-component cartridge 18 by means of a snap on type connection provided in the form of a cam 22. In use the cartridge 18 is filled with two-components, for example a hardener and a matrix material of a two-component adhesive (not shown). The mixing head 16 can be fixedly received within the mixer housing 12 by a press fit or by further attachment means such as snap fit connectors (not shown).

Figure 2A:
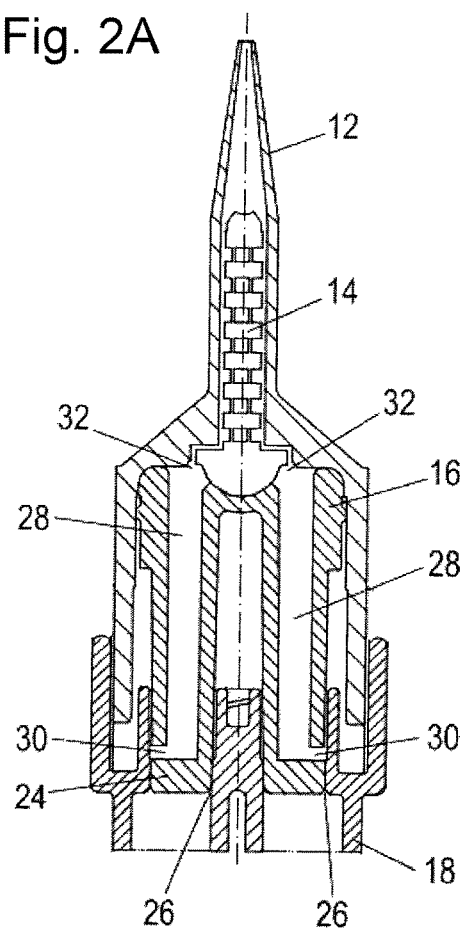
FIGS. 2A-2D are different positions of use of the syringe of FIG. 1.

FIG. 2A shows a part section through the syringe 10 of FIG. 1 in a first position of use of the syringe 10. The mixing head 16 is present in a sealed position in which a base 24 of the mixing head 16 is arranged in a plane of outlets 26 of the two-component cartridge 18 in order to seal the two-component cartridge 18. In this position no material can flow from the cartridge 18 into passages 28 of the mixing head 16 and thus no material can flow into the mixer housing 12 and come into contact with the mixing element 14 in the sealed position. As can clearly be seen the passages 28 present in the mixing head 16 substantially have an L-shape in a cross-section thereof, with the shorter limb of the passages 28 being present in the region of inlets 30 of the mixing head 16, whereas the outlets 32 of the mixing head 16 are arranged at the opposite end of the mixing head remote from the inlets 30. The passages 28 can also be considered as having a generally tubular shape with a lateral inlet 30.

In order to ensure a seal at the outlets 26 of the cartridge 18, the base 24 of the mixing head 16 can include a structure or means providing a seal. This means or structure can, for example, comprise a press fit between the base 24 and the outlets 26.

Figure 2B:
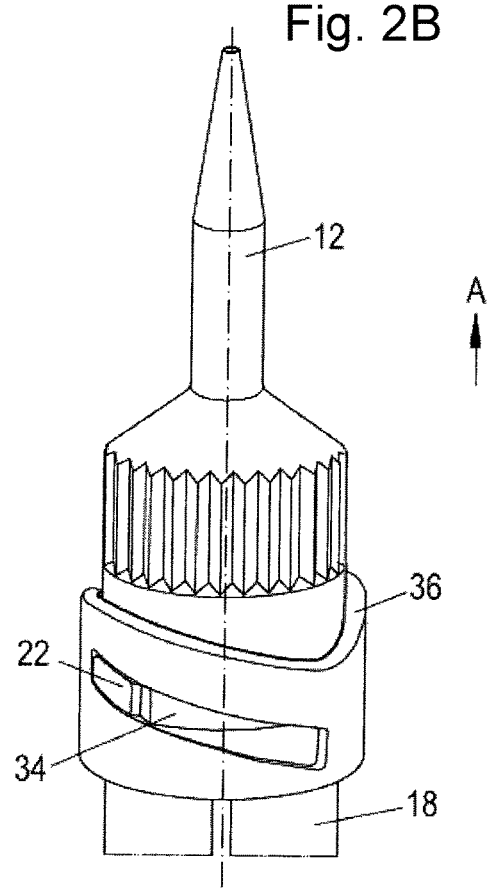

FIG. 2B shows a side view onto the syringe 10 of FIG. 2A. In this position the cam 22 engages the left hand upper part of a slot 34 disposed in a guide portion 36 of the cartridge 18. The slot 34 is disposed at an inclination with regard to a plane perpendicular to a dispensing direction A. As can be seen from a comparison of FIGS. 2A and 2C the mixing element 14 rotates with the mixer housing 12 relative to the mixing head 16 on a rotation from the sealed position into the dispensing position. This is because the mixing element 14 is compulsorily guided in the mixer housing 12.

Figure 2C:
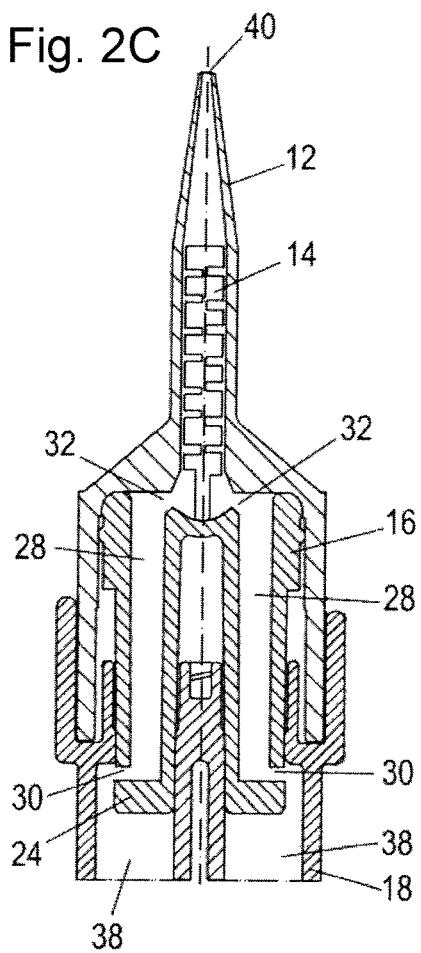

On a rotation of the mixer housing 12, i.e. on a movement of the cam 22 of FIG. 2B from the left to the right (see FIG. 2D) in the slot 34 disposed in the guide portion 36 of the cartridge 18, the syringe 10 is moved from the sealed position into a dispensing position as illustrated in FIG. 2C. During this movement the mixing head 16 is axially displaced downwardly in a direction opposite to the dispensing direction A. The inlets 30 of the passages 28 are now in fluid communication with chambers 38 of the cartridge 18. On an actuation of the plunger 20 (see e.g. FIG. 1) material (not shown) present in the chambers 38 can be discharged through the mixing head 16 via the mixing element 14 and out of an outlet 40 of the mixer housing 12.

Figure 2D:
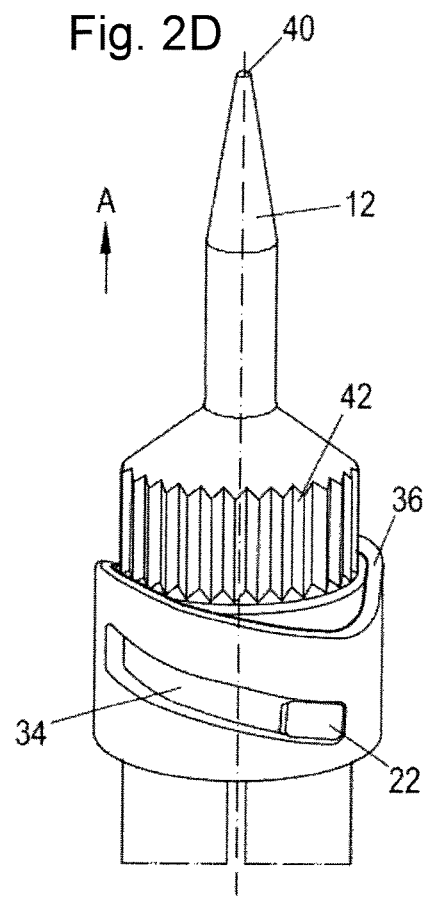

As can also be seen from a comparison of FIGS. 2B and 2D the mixer housing 12 is also axially displaced downwardly due to the compulsory guidance provided in the form of the cooperating cam 22 and slot 34. In order to facilitate the rotational movement of the mixer housing 12 this can include a profiled surface 42.

Figure 3:
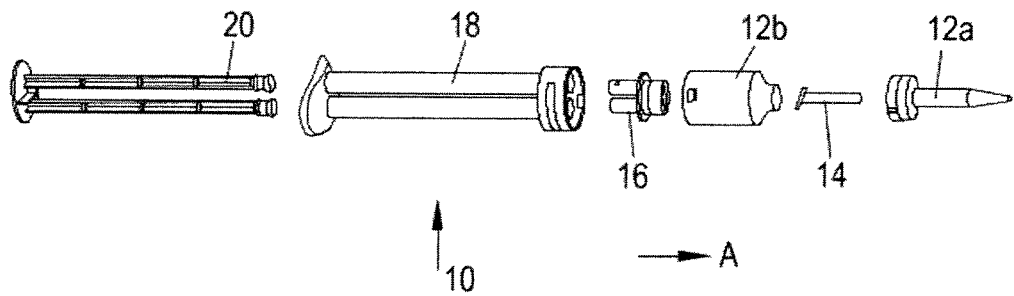
FIG. 3 is an exploded view of a second embodiment of a syringe.

FIG. 3 shows an exploded view of a further syringe 10. In this example the syringe 10 has a multi part housing 12 comprising at least a mixer housing cover 12a and a mixer housing base 12b. Moreover, the guide slot 34 of the compulsory guide runs in a plane substantially perpendicular to the dispensing direction A. Thus on a rotation of the mixer housing 12 and on a corresponding movement of the mixing head 16 from the sealed position into the dispensing position the mixer housing base 12b is not axially displaced, whereas the mixer housing cover 12a is axially displaced in a direction opposite to the dispensing direction A.

Like with the embodiment shown in FIG. 1, the mixing head 16 is also axially moved in order to take on the different positions of use (see FIGS. 4A to 4D).

FIGS. 4A to 4D illustrate how the mixer housing base 12b is rotated without axial displacement in or against the dispensing direction A on a shift from one position of use to the other, whereas the mixer housing cover 12a and the mixing head 16 are axially displaced.

The dispensing mechanism is however, the same as that shown in connection with FIGS. 1 to 2D.

Figure 4A:
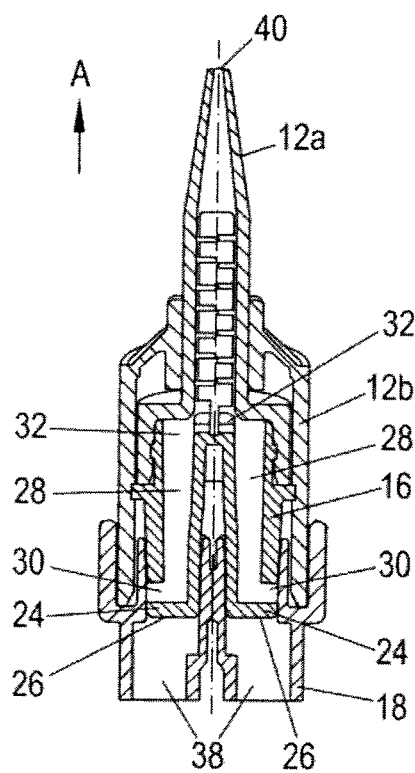
FIGS. 4A-4D are different positions of use of the syringe of FIG. 3.
Figure 4B:
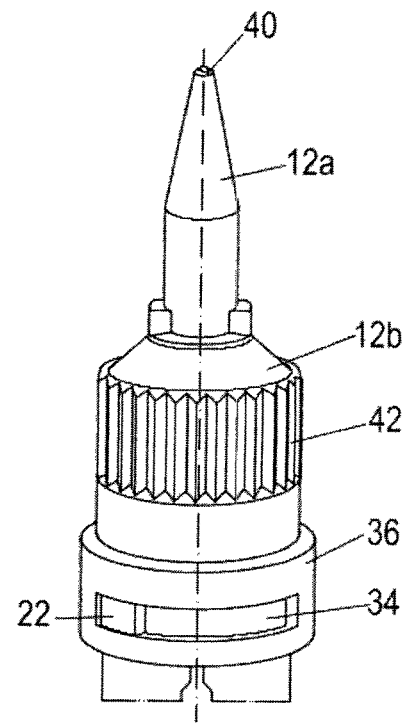
Figure 4C:
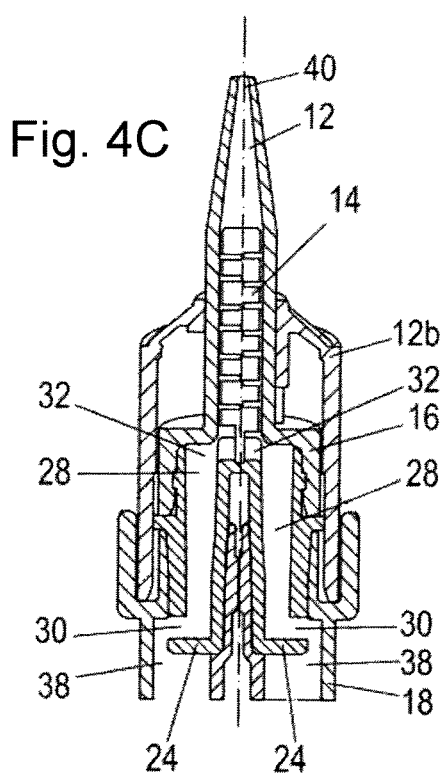
Figure 4D:
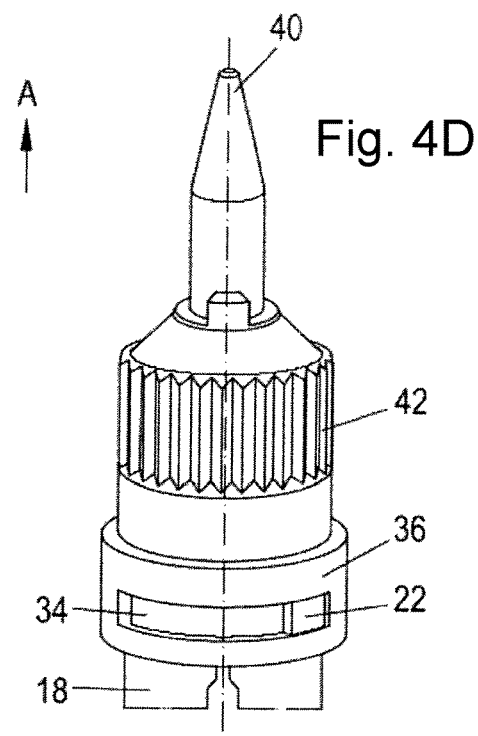

As can be seen from a comparison of FIGS. 4A and 4C the mixing element 14, the mixer housing cover 12a and the mixing head 16 do not rotate relative to one another on a rotation of the mixer housing base 12b from the sealed position into the dispensing position. This is because the mixer housing cover 12a, the mixing element 14 and the mixing head 16 are not rotated on rotational movement of the mixer housing base.

The axial displacement of the mixer housing cover 12a and the mixing head 16 is effected by ramps 44 present on an outside of the mixer housing cover 12a (FIG. 5A) cooperating with ramps 45 present on an inside of the mixer housing base 12b (FIG. 5B). These ramps 44, 45 are respectively inclined with respect to a plane perpendicular to the dispensing direction A and ensure the axial displacement of the mixing head 16 from the sealed position into the dispensing position in a direction opposite to the dispensing direction A upon a rotation of the mixer housing base 12b. In order to ensure a smooth continuous fine height adjustment two pairs of ramps 44 are provided off-set at even angular spacing in the circumferential direction of the mixer housing cover 12a and the mixer housing base 12b.

FIG. 6 shows an exploded view of a syringe 10. This syringe 10 can be moved between three positions of use, namely from a venting position (see FIGS. 7A and 7B) into a sealed position (see FIGS. 7C and &D) and from the sealed position into a dispensing position (see FIGS. 7E and 7F). FIGS. 6 and 7 show that the slot 34 also contains a region having an axial slot 49. This axial slot 49 is provided in order to move the syringe 10 from the venting position into the sealed position by engaging a press fit between the base 24 of the mixing head 16 and the outlets 26 of the multi-component cartridge 18.

Thus in order to effect the movement from the venting position into the sealed position the mixer housing 12 is first axially displaced downwardly in the axial slot 49. As can be seen from FIG. 7A the cam 22 is present in an axially raised position in the axial slot 49 in contrast to the position shown in FIG. 7C, in which the syringe 10 is present in the sealed position and the cam 22 is present in an axially lower position.

FIG. 7B shows that the mixing head 16 is in a position in which the base 24 of the mixing head 16 is raised with respect to e.g. the position shown in FIG. 7D, in which the mixing head 16 is present in the sealed position. In the position of FIG. 7B air present in the chambers 38 can escape passed the base 24 and out of the mixer housing 12 via the outlet 40 and also through sides of the mixer housing 12. A space 46 is present between the inner surfaces 48 of the outlets 26 of the cartridge 18 and the base 24 of the mixing head 16. This space 46 is dimensioned such that air can pass through this, but any material to be filled into the chambers 38 of the cartridge 18 cannot.

Moreover, the inner surface 48 of the outlets 26 are formed tapering towards the lower end of the outlets 26. This, on the one hand, ensures the press fit in the sealed position and thus the seal of the base 24 of the mixing head 16 in the outlets 26 of the multi-component cartridge 18. On the other hand, the increased diameter away from the lower end of the outlets 26 forms the space 46 through which the air present in the chambers 38 can escape in the venting position.

Moreover, a shoulder 47 can be disposed in the region of the lower end of the outlets 26 to ensure such a press fit and a tight seal at the outlets 26.

In this connection it must be noted that once the syringe 10 is in the sealed position or in the dispensing position, air or material present in the chambers 38 is generally not able to escape via the sides of the mixer housing 12 but is rather guided through the passages 28 present in the mixing head 16 and out through the outlet 40 of the mixer housing 12 via the mixing element 14.

On rotation of the mixer housing 12 from the sealed position shown in FIGS. 7C and 7D the cam 22 of the mixer housing 12 is moved along the inclined guide slot 34 into the position shown in FIGS. 7E and 7F. This method of employment is like that shown and described in conjunction with FIGS. 2A to 2D. Moreover, the mixing element 14 rotates with the mixer housing 12 relative to the mixing head 16 on a rotation from the sealed position into the dispensing position. This is because the mixing element 14 is compulsory guided in the mixer housing 12 on a rotation thereof.

FIG. 8 shows a view of a further syringe 10. Like the embodiment of FIG. 6 this syringe 10 can also be moved between three positions of use.

As illustrated the shift from the venting position (FIGS. 9A and 9B) into the sealed position (FIGS. 9C and 9D) is effected solely by a rotation of the mixer housing 12 in the guide slot 34. Whereas the shift from the sealed position into the dispensing position (FIGS. 9E and 9F) is effected first by an axial displacement of the mixer housing 12 downwardly and then a rotational movement along the z-shaped slot 51. This shape of the slot 51 is beneficial as it, on the one hand, ensures that the three different positions each have a defined point in the slot 51. On the other hand, having an axial jump followed by a further rotation allows the syringe 10 to be locked into the dispensing position and thereby prevents a movement back into the sealed position if a pressure is axially applied on the mixing head 16 during the dispensing. Moreover, the mixing element 14 rotates with the mixer housing 12 relative to the mixing head 16 on rotation from the venting position into the sealed position. This is because the mixing element 14 is also compulsory guided in the mixer housing 12 in this embodiment.

Having regard to the syringes 10 shown in FIGS. 6 to 9 these are usually filled by a user of the cartridge 18 with a mixing and dispensing apparatus already being connected to the cartridge 18. For this reason, they require the venting position, so that the air can be removed from the chambers 38 of the cartridge 18 on a filling thereof. Since the filling takes place from the end 50 (see FIG. 8) of the cartridge 18 remote from the mixer housing 12 the venting has to be provided in the region of the mixer housing 12.

Figure 10A:
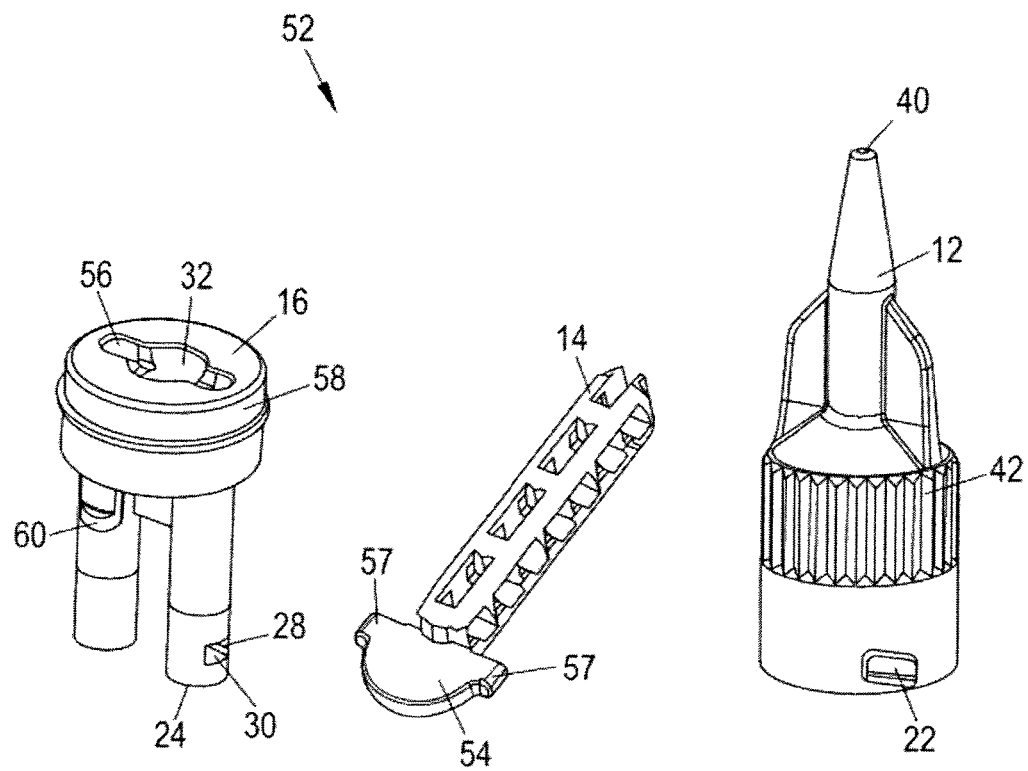
FIGS. 10A-10B are various parts of different embodiments of a mixing and dispensing apparatus.

FIG. 10A shows a mixing and dispensing apparatus 52 for multi-component materials, the apparatus comprising a mixer housing 12, a mixing element 14, and a mixing head 16. This mixing and dispensing apparatus 52 is typically used in a syringe 10 having two positions of use, a dispensing position and a sealed position. Alternatively this mixing head 16 can also be used in a syringe 10 having three positions of use. In this connection it should be noted that a base 54 of the mixing element 14 is partly received in a groove 56 provided in a top part 58 of the mixing head 16 and shoulders 57 of the mixing element 14 engage corresponding cut outs (not shown) provided in the mixer housing 12. Thereby the mixing element 14 is allowed to rotate in the groove 56 as the mixer housing 12 is rotated and rotates the mixing element 14. In the assembled state the mixing element 14 and the shoulders 57 thereof are received in the mixer housing 12 and the mixing head 16 is arranged adjacent to the mixing element 14, so that the base 54 of the mixing element 14 is received in the groove 56 and can rotate in the groove 56.

An orientation means or device 60 can be seen on a side of the mixing head 16, this is preferably configured in such a way that the mixing head 16 is connected to the mixer housing 12 in the assembled state of the mixing and dispensing apparatus 52 in the correct orientation by engaging a corresponding cut out (not shown) in the mixer housing 12.

Two outlets 32 of the mixing head 16 are further visible at a top 58 of the mixing head 16. These are in fluid communication with two passages 28, preferably two substantially L-shaped passages in a cross-section thereof, with the shorter limb of the L forming a lateral inlet 30 of the generally tubular passage 28 into the mixing head 16. When the mixing head 16 is in the dispensing position the inlets 30 of these passages 28 are also in fluid communication with the chambers 38 of a two-component cartridge 18 permitting a fluid flow (not shown) from the cartridges 18 via the mixing head 16, the mixing element 14 through, the mixer housing 12 and out of an outlet 40.

Figure 10B:
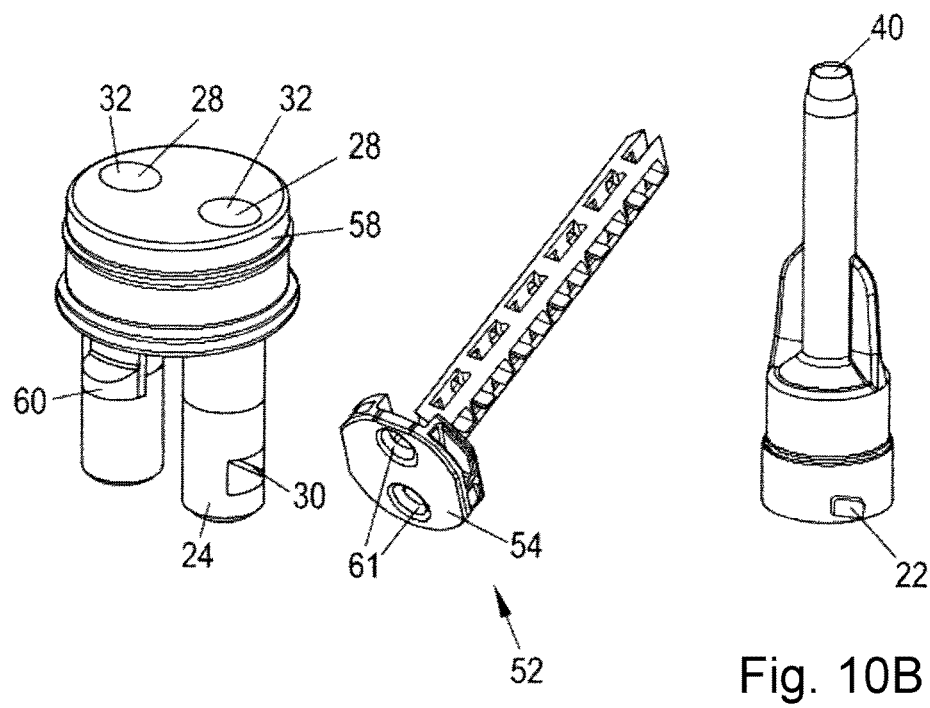

FIG. 10B shows a different version of the mixing and dispensing apparatus 52. The main difference to the version shown in FIG. 10A is that the mixing element 14 is not received in a groove of the mixing head 16 but rather only moves in cooperation with the mixer housing 12 relative to the mixing head 16. The mixing element 14 has two inlets 61. By rotating the mixing element 14 relative to the mixing head 16, the two inlets 61 can either be aligned with the outlets 32 of the mixing head 16 or can be closed in order to achieve a second seal in the region of the mixing element 14. This can be particularly beneficial if an additional seal is required.

The mixing head respectively shown in FIGS. 10A and 10B has a substantially U-shape cross section thereof. The ends of the shanks of the U can be configured to seal the outlets 26 of the cartridge 18 when the mixing and dispensing apparatus 52 is combined with a cartridge 18 (such as the ones shown in FIGS. 11A and 11B respectively) to form a syringe 10 and the syringe 10 is in the sealing position.

Figure 11A:
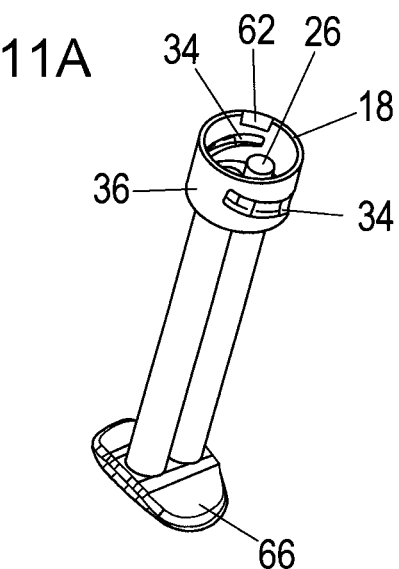
FIGS. 11A-11B are different embodiments of cartridges.

FIG. 11A shows a two-component cartridge 18, the cartridge 18 comprising a respective chamber 38 for one component of a multi-component material and a guide portion 36 having two guide slots 34. The guide portion 36 is typically integrally formed with the multi-component cartridge 18. The guide slot 34 is configured to facilitate a movement of a mixing and dispensing apparatus 52 connectable thereto between at least two positions of use. Two cut outs 62 are indicated in a top part of the guide portion 36. These cut outs 62 facilitate the introduction of a mixing and dispensing apparatus 52, such as the one shown in FIG. 10A, on the assembly to a syringe 10. These cut outs 62 are a part of the snap on mechanism used to, preferably fixedly, connect the mixing and dispensing apparatus 52 thereto.

Figure 11B:
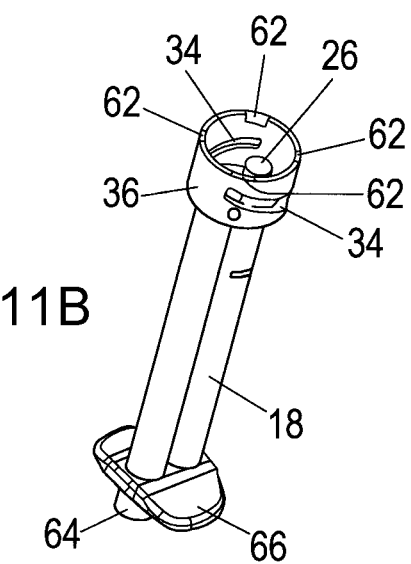

FIG. 11B shows a further type of two-component cartridge, the difference to the cartridge shown in FIG. 11A being that the inlets 64 to the chambers 38 of the cartridge 18 project beyond a base 66 of the cartridge 18. These inlets 64 can be adapted such that they can cooperate with e.g. a two-component cartridge as is disclosed in EP 0 730 913 whose contents is hereby included by reference. Thus, the base of the cartridge 18 can be equipped with coded alignment means such as bayonet lugs, cut outs and noses adapted to cooperate with such a multi-component cartridge. Corresponding markings can be provided on the plunger 20 in order to ensure that this is correctly installed if the cartridge 18 is adapted for multiple uses, in order to avoid a cross-contamination between the plunger 20 and the cartridge 18.

The cartridges 18 illustrated in FIGS. 11A and 11B are so-called 1:1 cartridges 18, but can easily be replaced by 2:1, 4:1 and 10:1 cartridges 18, depending on the desired use and materials used.

Moreover, markings are disposed on the cartridge 18 to indicate which position of use a syringe 10 having such a cartridge is currently in. Also shown are further introduction cut outs 62 to facilitate the introduction of a mixing and dispensing apparatus 52, such as the one shown in FIG. 10B on the assembly to a syringe 10. These can have the shape of ramps in order to facilitate the insertion of the mixing and dispensing apparatus 52.

The mixing and dispensing apparatus 52 can also include such markings to obtain a coded alignment of this with respect to the cartridge 18. This means that the mixing and dispensing apparatus 52 preferably can only be connected to the cartridge 18 in one direction.

The cut outs 62 shown in FIGS. 11A and 11B can be provided symmetrically or asymmetrically if a coded alignment of the mixing and dispensing apparatus 52 relative to the cartridge 18 is desired.

It should further be noted that the components shown in FIGS. 1 to 5D, 10A and 11A are typically used for small volume syringes 10, having a volume in the range of 0.1 to 2 ml. The cartridges 18 of these small volume syringes 10 are typically filled with the mixing head 16, the mixing element 14 and the mixer housing 12 being removed. These are then typically attached once the cartridges 18 have been filled. Thus, no venting is required as the cartridges 18 can be filled by a negative pressure arising when the plungers 20 are pulled out of the cartridges 18 on a filling thereof.

In contrast to this, components shown in the FIGS. 6 to 9F, 10B and 11B are typically used with larger volume syringes 10 typically having a volume in the range of 1.5 to 5 ml. These syringes 10 are usually filled by a user of the cartridge 18 and the specific amount to be used is filled on the time of filling. For this purpose the mixing and dispensing apparatus 52 is typically already connected to the cartridge 18 of the syringe and is connected to a two-component reservoir at the end 50 remote to the mixing and dispensing apparatus 52. The two-component reservoir can be provided having the form of a two-component cartridge, such as the one described in EP 0 730 913 B1.

In the framework of this invention it should be noted that the mixing head 16 is considered to be a component which can act at least as a sealing element, and as a guide element and preferably also as a venting element. When acting as a sealing element the mixing head 16 seals the outlets 26 of a cartridge 18. When acting as a guide element it permits the passage of substances stored in the cartridge 18 via the outlets 26 to the mixing element 14, wherein it guides the substances in respective passages 28 without the substances contacting one another over at least a substantial part of the length of the mixing head 16. In the region of the one end of the mixing head 16 remote from the inlets 30, the mixing head 16 can comprise a region having two outlets 32 through which the substances are guided towards one another so that they can be forced into engagement in the region of the mixing element 14. Alternatively, the guiding of the substances towards one another can take place outside of the mixing head. On a filling of the cartridge 18 the mixing head 16 can be positioned such that it fulfills a venting action.

It should be noted that the individual components of the various syringes 10 can all be fabricated in an injection molded process from a diverse range of plastics. The plastic may have to be specifically adapted to the multi-component material stored therein in order to avoid a chemical reaction therebetween and a contamination resulting therefrom.

What is claimed is:

1. A single fill syringe for multi-component materials, comprising:
    a mixer housing;
    a mixing element;
    a multi-component cartridge; and
    a mixing head separate from the mixer housing, the mixing head being arranged at least partly within the mixer housing and adjacent to the multi-component cartridge, and arranged to be moveable in an axial direction of the syringe between at least two positions, the at least two positions comprising a sealed position and a dispensing position, the movement in the axial direction of the mixing head being brought about by a rotation of at least a part of the mixer housing relative to the multi-component cartridge, and the mixing head being axially displaced in a direction opposite to a dispensing direction on displacement of the mixing head from the sealed position into the dispensing position, the syringe configured to be activated upon displacement of the mixing head from the sealed position to the dispensing position by the rotation of the at least a part of the mixer housing relative to the multi-component cartridge and with at least a part of a base of the mixing head being a seal and being configured to seal outlets of the multi-component cartridge when the mixing head is in the sealed position, rotation of the mixer housing causing axial displacement of at least a part of the mixer housing and the mixing head relative to the multi-component cartridge.

2. The syringe in accordance with claim 1, wherein the mixing head at least partly projects into the multi-component cartridge in the dispensing position.

3. The syringe in accordance with claim 1, wherein the mixing head comprises a plurality of passages for the multi-component materials to be dispensed, and a material to be dispensed only enters the plurality of passages when the mixing head is in the dispensing position.

4. The syringe in accordance with claim 3, wherein the mixing head comprises two or more substantially L-shaped passages in a cross-section thereof and material to be dispensed only enters the two or more passages through a short shank of the substantially L-shaped passages when the mixing head is in the dispensing position.

5. The syringe in accordance with claim 3, wherein the multi-component cartridge includes chambers, and each of the plurality of passages of the mixing head projects at least partly into a respective chamber of the chambers of the multi-component cartridge in the dispensing position to form a fluid connection between the plurality of passages and the chambers.

6. The syringe in accordance with claim 3, wherein the mixing head comprises a mixing portion connecting the plurality of passages and being configured to permit a fluid flow to the mixing element.

7. The syringe in accordance with claim 2, wherein the mixer housing is non-releasably connected to the multi-component cartridge.

8. The syringe in accordance with claim 1, wherein the mixer housing is connected to the multi-component cartridge by a bayonet like connection or a snap on type connection.

9. The syringe in accordance with claim 1, wherein elements are configured to prevent movement of the mixing head from the dispensing position into the sealed position.

10. The syringe in accordance with claim 1, wherein the mixer housing includes two parts, with the two parts being axially moveable with respect to one another.

11. The syringe in accordance with claim 10, wherein the movement in the axial direction is effected by cooperating ramps present at each of the two parts.

12. The syringe in accordance with claim 1, wherein the mixing head is capable of being disposed in a further axial position, a venting position, with the venting position preferably being provided for filling of the multi-component cartridge.

13. The syringe in accordance with claim 12, wherein the movement of the mixing head from the venting position into the sealed position is effected by at least one of axial movement of at least a part of the mixer housing and rotation of the mixer housing relative to the multi-component cartridge.

14. The syringe in accordance claim 1, wherein the multi-component cartridge is filled with substances.

15. A syringe, comprising:
    a mixer housing;
    a mixing element;
    a multi-component cartridge;
    a mixing head separate from the mixer housing, the mixing head being arranged at least partly within the mixer housing and adjacent to the multi-component cartridge, and arranged to be moveable in an axial direction of the syringe between at least two positions, the at least two positions comprising a sealed position and a dispensing position, the movement in the axial direction of the mixing head being brought about by a rotation of at least a part of the mixer housing relative to the multi-component cartridge, and the mixing head being axially displaced in a direction opposite to a dispensing direction on displacement of the mixing head from the sealed position into the dispensing position, the syringe configured to be activated upon displacement of the mixing head from the sealed position to the dispensing position by the rotation of the at least a part of the mixer housing relative to the multi-component cartridge and with at least a part of a base of the mixing head being a seal and being configured to seal outlets of the multi-component cartridge when the mixing head is in the sealed position; and
    a guide portion having at least one guide slot associated with the multi-component cartridge, the guide portion being fixedly connected to or integrally formed with the multi-component cartridge, and the mixer housing includes at least one cam cooperating with the at least one guide slot to facilitate rotational movement or the movement in the axial direction between the sealed position and the dispensing position.

16. The syringe in accordance with claim 15, wherein the mixing head at least partly projects into the multi-component cartridge in the dispensing position.

17. The syringe in accordance with claim 16, wherein the mixer housing is non-releasably connected to the multi-component cartridge.

18. The syringe in accordance with claim 15, wherein the mixing head comprises a plurality of passages for the multi-component materials to be dispensed, and a material to be dispensed only enters the plurality of passages when the mixing head is in the dispensing position.

19. The syringe in accordance with claim 18, wherein the multi-component cartridge includes chambers, and each of the plurality of passages of the mixing head projects at least partly into a respective chamber of the chambers of the multi-component cartridge in the dispensing position to form a fluid connection between the plurality of passages and the chambers.

20. The syringe in accordance with claim 19, wherein the mixing head comprises two or more substantially L-shaped passages in a cross-section thereof and material to be dispensed only enters the two or more passages through a short shank of the substantially L-shaped passages when the mixing head is in the dispensing position.

21. The syringe in accordance with claim 18, wherein the mixing head comprises a mixing portion connecting the plurality of passages and being configured to permit a fluid flow to the mixing element.

22. The syringe in accordance with claim 15, wherein the mixer housing is connected to the multi-component cartridge by a bayonet like connection or a snap on type connection.

23. The syringe in accordance with claim 15, wherein elements are configured to prevent movement of the mixing head from the dispensing position into the sealed position.

24. The syringe in accordance with claim 15, wherein rotation of the mixer housing causes axial displacement of at least a part of the mixer housing and the mixing head relative to the multi-component cartridge.

25. The syringe in accordance with claim 15, wherein the mixer housing includes two parts, with the two parts being axially moveable with respect to one another.

26. The syringe in accordance with claim 25, wherein the movement in the axial direction is effected by cooperating ramps present at each of the two parts.

27. The syringe in accordance with claim 15, wherein the mixing head is capable of being disposed in a further axial position, a venting position, with the venting position preferably being provided for filling of the multi-component cartridge.

28. The syringe in accordance with claim 27, wherein the movement of the mixing head from the venting position into the sealed position is effected by at least one of axial movement of at least a part of the mixer housing and rotation of the mixer housing relative to the multi-component cartridge.

29. The syringe in accordance claim 15, wherein the multi-component cartridge is filled with substances.

* * * * *